(12) United States Patent
Tzfira et al.

(10) Patent No.: US 7,659,447 B2
(45) Date of Patent: Feb. 9, 2010

(54) INCREASING HOST PLANT SUSCEPTIBILITY TO AGROBACTERIUM INFECTION BY OVEREXPRESSION OF THE ARABIDOPSIS VIP1 GENE

(76) Inventors: Tzvi Tzfira, 84 N. Counrty Rd., #C10, Port Jefferson, NY (US) 11777; Vitaly Citovsky, 5 Lindsey Pl., Commack, NY (US) 11725

( * ) Notice: Subject to any disclaimer, the term of this patent is extended or adjusted under 35 U.S.C. 154(b) by 962 days.

(21) Appl. No.: 10/434,968

(22) Filed: May 9, 2003

(65) Prior Publication Data
US 2003/0233676 A1 Dec. 18, 2003

Related U.S. Application Data

(60) Provisional application No. 60/379,285, filed on May 9, 2002.

(51) Int. Cl.
C12N 15/82 (2006.01)
A01H 5/00 (2006.01)
C07H 21/04 (2006.01)

(52) U.S. Cl. ............ 800/294; 800/295; 800/298; 800/278; 435/419; 435/468; 435/320.1; 536/23.6

(58) Field of Classification Search ............ 435/320.1
See application file for complete search history.

(56) References Cited

U.S. PATENT DOCUMENTS

2003/0233676 A1* 12/2003 Tzfira et al. ............ 800/279

FOREIGN PATENT DOCUMENTS

| EP | 1 033 405 A | 9/2000 |
|---|---|---|
| EP | 1 033 405 A2 * | 9/2000 |
| WO | WO 01/20012 A | 3/2001 |
| WO | WO 03/013227 A | 2/2003 |
| WO | WO 03/014327 A | 2/2003 |

OTHER PUBLICATIONS

Tzfira, et al. (2001), VIP1, an *Arabidopsis* protein that interacts with *Agrobacterium* VirE2, is involved in VirE2 nuclear import and *Agrobacterium* infectivity. EMBO J. pp. 3596-3607.*
Fridy et al. Cloning and characterization of two human VIP1-like inositol hexakisphosphate and diphosphoinositol pentakisphosphate kinases. (2007) JBC, vol. 282, pp. 30754-30762.*
Kircher et al. CPRF4a, a novel plant bZIP protein of the CPRF family: comparative analyses of light-dependent expression,post-transcriptional regulation, nuclear import and heterodimerisation. (1998) MGG; vol. 257; pp. 595-605.*
Zhou et al. Identification of a novel gene encoding a p53-associated protein. (1999) Gene; vol. 235, pp. 93-101.*
Tzfira et al (The EMBO Journal (2001) vol. 20; pp. 3596-3607.*
GenBank Accession AF225983 *Arabidopsis thaliana* VirE2-interacting protein VIP1 mRNA, complete cds. (2001); pp. 1-2.*
GenBank Accession AC009526 *Arabidopsis thaliana* chromosome I BAC F2J6 genomic sequence, complete sequence. (2000); pp. 1-36.*

Filichkin et al. (1993) "Formation of a putative relaxation intermediate during T-DNA processing directed by the *Agrobacterium tumefaciens* VirD1, D2 endonuclease" *Molecular Microbiology*, 8(5):915-926.
Relic et al. (1998) "Interaction of the DNA modifying proteins VirD1 and VirD2 of *Agrobacteritun tumefaciens* : Analysis by subcellular localization in mammalian cells" *Proc. Natl. Acad. Sci USA*, 95:9105-9110.
Tzfira et al. (2001) "VIP1, An *Arabidopsis* protein that interacts with *Agrobacterium* VirE2, is involved in VirE2 nuclear import and *Agrobacterium* infectivity". *The EMBO Journal*, 20(13):3596-3607.
Tzfira et al. (1997) "Transgenic *Populus tremula*: a step-by-step protocol for its *Agrobacterium*-mediated transformation" *Plant Molecular Biology Reporter* 15:219-235.
Ward et al. (2002) "*Agrobacterium* VirE2 gets the VIP1 treatment in plant nuclear import" *Trends in Plant Science*, 7(1);1-3.
Tzfira Tzvi t et al., (Aug. 6, 2002) "Increasing Plant Susceptibility to *Agrobacterium* Infection by Overexpression of the *Arabidopsis* Nuclear Protein VIP1"; *Proc. Nat. Sci.* vol. 99 (16): 10435-10440.
Ballas Nurit et al., (1997) "Nuclear Localization Signal Binding Protein From *Arabidopsis* Mediates Nuclear Input Import of *Agrobacterium* VIRD2 Protein"; *Proc. Nat. Sci.* vol. 94(20): 10723-10728.
Deng Wanyin et al., (Jun. 9, 1998) "*Agrobacterium* VIRD2 Protein Interacts With Plant HOS Cyclophilins"; *Proc. Nat. Sci*, (95): 7040-7045.
Gelvin Stanton B. et al., (2000) "*Agrobacterium* and Plant Genes Involved in T-DNA Transfer and Integration"; *Ann. Rev. Phys. Molec. Bio.*, pp. 223-256.
"NSF Agrobacterium Genomics Grant Progress Report May 2002"; retrieved from internet: http://www.biology.purdue.edu/people/faculty/gelivnweb/2002activities.htm_1.
"Identification of Plant Genes Involved in *Agrobacterium*-Mediate Dtransformation"; retrieved from internet: http://www.bio.purdue.edu/people/faculty/gelvin/gelvinweb/completeproposal.html.
Tzfira Tzvi et al., (Mar. 2002) "Partners-In-Infection: Host Proteins Involved in the Transformation of Plant Cells by *Agrobacterium*"; *Trends in Cell Bio.*, vol. 12 (3) 121-129.
Tzfira Tzvi et al., (2002) "Nucleic Acid Transport in Plant-Microbe Interactions;The Molecules That Walk Through the Walls"; *Ann. Rev. Micro. Biol.*, pp. 187-219.
Tzfira Tzvi et al., "From Host Recognition to T-DNA Integration: The Function of Bacterial and Plant Genes in the *Agrobacterium*-Plant Cell Interation"; *Molec. Plant Path.*, 1 (4) 201-212.

* cited by examiner

*Primary Examiner*—Cathy Kingdon Worley
(74) *Attorney, Agent, or Firm*—Ann R. Pokalsky, Esq.; Dilworth & Barrese

(57) ABSTRACT

The present invention is directed to methods and compositions which employ an *Arabidopsis* VIP1 gene or VIP1-like gene from another plant species for purposes of increasing host plant susceptibility to *Agrobacterium* infection. Methods for increasing susceptibility of a host to *Agrobacterium* infection and methods for improving *Agrobacterium*-mediated gene transfer are provided. Also provided are chimeric genes and expression vectors that, upon introduction into a plant cell, enable the plant cell to become more susceptible to *Agrobacterium* infection and thus better transformed via *Agrobacterium*-mediated gene transfer. Transgenic plant cells and plants regenerated therefrom which overexpress a VIP1 or VIP1-like gene are also provided.

22 Claims, 9 Drawing Sheets cDNA Sequence Agrobacterium VirE2 Interactor, VIP1, from Arbidopsis

```
1   atg tcc gtt gat tcg gaa gaa acc tca tcg aac ggt gtt gtt cct cct aat tct ctt cct   (SEQ ID NO:1)
1   M   S   V   D   S   E   E   T   S   S   N   G   V   V   P   P   N   S   L   P     (SEQ ID NO:2)
61  cca aaa ccc gaa gct aga ttc ggt cgc cat gtt cgt agc ttc tcg gtt gat tcc gat ttc
21  P   K   P   E   A   R   F   G   R   H   V   R   S   F   S   V   D   S   D   F
121 ttc gat gat ttg ggt gtt act gag gag aag ttt ata gct acc agt tca gga gag aag aag
41  F   D   D   L   G   V   T   E   E   K   F   I   A   T   S   S   G   E   K   K
181 aaa ggg aat cat cat cat agc agg agt aat tct atg gat gga gag atg agt tcg gcg tcg
61  K   G   N   H   H   H   S   R   S   N   S   M   D   G   E   M   S   S   A   S
241 ttt aat atc gaa tcg att tta gct tct gtg agt ggt aaa gat agt ggg aag aag aat atg
81  F   N   I   E   S   I   L   A   S   V   S   G   K   D   S   G   K   K   N   M
301 gtc atg ggt ggt gat aga ctt gct gag ctt gct att ctt gat cct aaa aga gct aaa agg
101 G   M   G   G   D   R   L   A   E   L   A   L   L   D   P   K   R   A   K   R
361 att tta gcg aat aga caa tct gcg gcg agg tcg aaa gag agg aag att agg tat act ggt
121 I   L   A   N   R   Q   S   A   A   R   S   K   E   R   K   I   R   Y   T   G
421 gag tta gag agg aag gtt cag aca ctt cag aat gaa gct act aca ttg tct gct caa gtc
141 E   L   E   R   K   V   Q   T   L   Q   N   E   A   T   T   L   S   A   Q   V
481 act atg tta cag aga gga aca tca gag ctg aac act gaa aat aaa cac ctc aaa atg cgg
161 T   M   L   Q   R   G   T   S   E   L   N   T   E   N   K   H   L   K   M   R
```

```
                                                                                              (SEQ ID NO:1)
                                                                                       A      (SEQ ID NO:2)
541 ctt caa gct tta gag caa caa gct gaa ctt agg gat gct ttg aat gaa gcg ctg cgg gat
181  L   Q   A   L   E   Q   Q   A   E   L   R   D   A   L   N   E   A   L   R   D
601 gaa ctg aac cga ctt aag gta gct gga gaa att cct cag ggg aat gga aat tct tac
201  E   L   N   R   L   K   V   A   G   E   I   P   Q   G   N   G   N   S   Y
661 aac cgt gct caa ttc tca cag caa tcg gca atg aat cag ttt ggg aac aaa acg aac
221  N   R   A   Q   F   S   Q   Q   S   A   M   N   Q   F   G   N   K   T   N
721 caa cag atg agt aca aac ggg cag cca tcg ctc cca agc tac atg gat ttc acc aag aga
241  Q   Q   M   S   T   N   G   Q   P   S   L   P   S   Y   M   D   F   T   K   R
781 ggc tgagttcgtgtcacctatatatgttgctgagttataaatacgttatattcattcgggctgcaatatttgatgt
261  G
859 atgtaaaaagtatgtatccatgtatatatgcttttgtgttgttagcgtctatgcagatatgttcatggcgacatc
938 ggtctacttttacaagtagtatccattgtaatatactacccaaaaaaaaaaaaaaaaaa
```

Arabidopsis Chromosome I, GenBank Accession Number AC009526

SEQUENCE LISTING

```
<160> NUMBER OF SEQ ID NOS: 2

<210> SEQ ID NO 1
<211> LENGTH: 999
<212> TYPE: DNA
<213> ORGANISM: Agrobacterium tumefaciens
<220> FEATURE:
<221> NAME/KEY: CDS
<222> LOCATION: (1)..(783)

<400> SEQUENCE: 1 atg tcc gtt gat tcg gaa gaa acc tca tcg aac ggt gtt gtt cct cct      48
Met Ser Val Asp Ser Glu Glu Thr Ser Ser Asn Gly Val Val Pro Pro
1               5                   10                  15 aat tct ctt cct cca aaa ccc gaa gct aga ttc ggt cgc cat gtt cgt      96
Asn Ser Leu Pro Pro Lys Pro Glu Ala Arg Phe Gly Arg His Val Arg
            20                  25                  30 agc ttc tcg gtt gat tcc gat ttc ttc gat gat ttg ggt gtt act gag     144
Ser Phe Ser Val Asp Ser Asp Phe Phe Asp Asp Leu Gly Val Thr Glu
        35                  40                  45 gag aag ttt ata gct acc agt tca gga gag aag aag aaa ggg aat cat     192
Glu Lys Phe Ile Ala Thr Ser Ser Gly Glu Lys Lys Lys Gly Asn His
    50                  55                  60 cat cat agc agg agt aat tct atg gat gga gag atg agt tcg gcg tcg     240
His His Ser Arg Ser Asn Ser Met Asp Gly Glu Met Ser Ser Ala Ser
65                  70                  75                  80 ttt aat atc gaa tcg att tta gct tct gtg agt ggt aaa gat agt ggg     288
Phe Asn Ile Glu Ser Ile Leu Ala Ser Val Ser Gly Lys Asp Ser Gly
                85                  90                  95 aag aag aat atg ggt atg ggt ggt gat aga ctt gct gag ctt gct ttg     336
Lys Lys Asn Met Gly Met Gly Gly Asp Arg Leu Ala Glu Leu Ala Leu
            100                 105                 110 ctt gat cct aaa aga gct aaa agg att tta gcg aat aga caa tct gcg     384
Leu Asp Pro Lys Arg Ala Lys Arg Ile Leu Ala Asn Arg Gln Ser Ala
```

```
                115                 120                 125
gcg agg tcg aaa gag agg aag att agg tat act ggt gag tta gag agg       432
Ala Arg Ser Lys Glu Arg Lys Ile Arg Tyr Thr Gly Glu Leu Glu Arg
    130                 135                 140 aag gtt cag aca ctt cag aat gaa gct act aca ttg tct gct caa gtc       480
Lys Val Gln Thr Leu Gln Asn Glu Ala Thr Thr Leu Ser Ala Gln Val
145                 150                 155                 160 act atg tta cag aga gga aca tca gag ctg aac act gaa aat aaa cac       528
Thr Met Leu Gln Arg Gly Thr Ser Glu Leu Asn Thr Glu Asn Lys His
                165                 170                 175 ctc aaa atg cgg ctt caa gct tta gag caa caa gct gaa ctt agg gat       576
Leu Lys Met Arg Leu Gln Ala Leu Glu Gln Gln Ala Glu Leu Arg Asp
            180                 185                 190 gct ttg aat gaa gcg ctg cgg gat gaa ctg aac cga ctt aag gtg gta       624
Ala Leu Asn Glu Ala Leu Arg Asp Glu Leu Asn Arg Leu Lys Val Val
        195                 200                 205 gct gga gaa att cct cag ggg aat gga aat tct tac aac cgt gct caa       672
Ala Gly Glu Ile Pro Gln Gly Asn Gly Asn Ser Tyr Asn Arg Ala Gln
    210                 215                 220 ttc tca tct cag caa tcg gca atg aat cag ttt ggg aac aaa acg aac       720
Phe Ser Ser Gln Gln Ser Ala Met Asn Gln Phe Gly Asn Lys Thr Asn
225                 230                 235                 240 caa cag atg agt aca aac ggg cag cca tcg ctc cca agc tac atg gat       768
Gln Gln Met Ser Thr Asn Gly Gln Pro Ser Leu Pro Ser Tyr Met Asp
                245                 250                 255 ttc acc aag aga ggc tgagttcgtg tcacctatat atgtttgctg agttataaat       823
Phe Thr Lys Arg Gly
            260 acgttatatt catttcgggc tgcaatattt gatgtatgta aaaagtatgt atgtatccat     883 gtataatggc ttttgtgttg ttagcgtcta tgcagatatg ttcatggcga catcggtcta     943 cttttacaag tagtatccat tgtaatatac taccccaaaa aaaaaaaaaa aaaaaa         999

<210> SEQ ID NO 2
<211> LENGTH: 261
<212> TYPE: PRT
<213> ORGANISM: Agrobacterium tumefaciens

<400> SEQUENCE: 2

Met Ser Val Asp Ser Glu Glu Thr Ser Ser Asn Gly Val Val Pro Pro
1               5                   10                  15

Asn Ser Leu Pro Pro Lys Pro Glu Ala Arg Phe Gly Arg His Val Arg
            20                  25                  30

Ser Phe Ser Val Asp Ser Asp Phe Phe Asp Asp Leu Gly Val Thr Glu
        35                  40                  45

Glu Lys Phe Ile Ala Thr Ser Ser Gly Glu Lys Lys Lys Gly Asn His
    50                  55                  60

His His Ser Arg Ser Asn Ser Met Asp Gly Glu Met Ser Ala Ser
65                  70                  75                  80

Phe Asn Ile Glu Ser Ile Leu Ala Ser Val Ser Gly Lys Asp Ser Gly
                85                  90                  95

Lys Lys Asn Met Gly Met Gly Gly Asp Arg Leu Ala Glu Leu Ala Leu
            100                 105                 110

Leu Asp Pro Lys Arg Ala Lys Arg Ile Leu Ala Asn Arg Gln Ser Ala
        115                 120                 125

Ala Arg Ser Lys Glu Arg Lys Ile Arg Tyr Thr Gly Glu Leu Glu Arg
    130                 135                 140
```

-continued

```
Lys Val Gln Thr Leu Gln Asn Glu Ala Thr Thr Leu Ser Ala Gln Val
145                 150                 155                 160

Thr Met Leu Gln Arg Gly Thr Ser Glu Leu Asn Thr Glu Asn Lys His
                165                 170                 175

Leu Lys Met Arg Leu Gln Ala Leu Glu Gln Gln Ala Glu Leu Arg Asp
            180                 185                 190

Ala Leu Asn Glu Ala Leu Arg Asp Glu Leu Asn Arg Leu Lys Val Val
        195                 200                 205

Ala Gly Glu Ile Pro Gln Gly Asn Gly Asn Ser Tyr Asn Arg Ala Gln
    210                 215                 220

Phe Ser Ser Gln Gln Ser Ala Met Asn Gln Phe Gly Asn Lys Thr Asn
225                 230                 235                 240

Gln Gln Met Ser Thr Asn Gly Gln Pro Ser Leu Pro Ser Tyr Met Asp
                245                 250                 255

Phe Thr Lys Arg Gly
            260
```

INCREASING HOST PLANT SUSCEPTIBILITY TO AGROBACTERIUM INFECTION BY OVEREXPRESSION OF THE ARABIDOPSIS VIP1 GENE

CROSS-REFERENCE TO RELATED APPLICATIONS

This application claims priority to U.S. Provisional application 60/379,285 filed May 9, 2002 which is incorporated by reference herein.

STATEMENT OF GOVERNMENTAL INTEREST

The present invention was made with support from the United States Government (grant No. 98-35304-6680 from the USDA, grant No. DBI-9975715 from NSF, and grant No. Q304X from NYSSTF). The U.S. Government may have certain rights in the invention.

BACKGROUND OF THE INVENTION

*Agrobacterium* elicits neoplastic growths on many plant species. This genetic modification results from the transfer and integration into the plant genome of a single-stranded copy (T-strand) of the bacterial transferred DNA (T-DNA) from the bacterial tumor-inducing (Ti) plasmid. In planta expression of several oncogenic genes encoded by the T-DNA leads to formation of tumors[1] and production and secretion of specific amino acid and sugar phosphate derivatives (opines) which are then exclusively utilized by the bacterium as a carbon/nitrogen source. Plant genetic transformation by *Agrobacterium* requires the presence of two genetic components located on the bacterial Ti plasmid: (i) T-DNA, the actual genetic element transferred into the plant cell genonme, and (ii) the virulence (vir) region composed of seven major loci (virA, virB, virC, virD, virE, virG, and virH), encoding most components of the protein machinery mediating T-DNA transfer (recently reviewed in refs. 2, 3-5).

The ability of *Agrobacterium* to infect eukaryotic cells is not limited to plants, and, in laboratory conditions, *Agrobacterium* has been shown to genetically transform yeast[6-8], filamentous fungi and cultivated mushrooms[9], and human cells[10]. Thus, *Agrobacterium* has been utilized as a model organism capable of a wide-range trans-kingdom DNA transfer. Furthermore, disarmed *Agrobacterium* strains that lack the wild type T-DNA, are widely used in plant genetic engineering[11-13]. One of the long-standing goals of these basic scientific and applied aspects of the *Agrobacterium* research is the increase of the transformation efficiency. To date, this objective has been addressed by modifying the *Agrobacterium* itself, e.g., introducing multiple copies of various vir genes[14-16], or by optimizing tissue culture and inoculation techniques[17].

While only the wild-type *Agrobacterium* T-DNA carries tumor-inducing genes, any DNA placed between the T-DNA borders will be transported into the plant cell nucleus (reviewed in ref. 19). This lack of sequence specificity implies that a T-DNA molecule itself does not contain specific signals for nuclear import and integration. Instead, this process is likely mediated by two *Agrobacterium* proteins, VirD2 and VirE2, which are thought to directly associate with the T-strand, forming a transport (T) complex[20, 21]. VIP1 (VirE2-interacting protein 1) is a recently discovered *Arabidopsis* protein, which is required for *Agrobacterium* infection.[18] Nuclear import of the T-complex is most likely assisted by VIP1 that specifically interacts with VirE2[18] and may mediate its interaction with the nuclear import machinery of the host cell[22].

Prior to the present invention, no endogenous host factors have been described that improve the *Agrobacterium*-mediated gene transfer. The present invention provides methods for increasing host susceptibility to *Agrobacterium* infection by overexpressing in the host, the *Arabidopsis* VIP1 or other VIP1-like gene.

SUMMARY OF THE INVENTION

The present invention provides a method of increasing susceptibility of a host cell to *Agrobacterium* infection. The method comprises the steps of introducing into a host cell, a nucleotide sequence encoding VIP1 or VIP1-like protein operably linked to a promoter which directs expression of the nucleotide sequence encoding VIP1 or VIP1-like protein in the host cell. The host cell can include any eukaryotic cell, such as insect, fungal, plant, or animal cell. Preferably, the host cell is a plant cell. Even more preferably, the plant cell is from a monocotyledonous plant species. Host cells made increasingly susceptible to *Agrobacterium* infection are thus better transformed via *Agrobacterium*-mediated gene transfer.

In an alternative embodiment, a method of increasing susceptibility of a host cell to *Agrobacterium* infection comprises the steps of introducing into a host cell, a nucleotide sequence encoding a protein which interacts with the *Agrobacterium* protein VirD2. Preferably, the nucleotide sequence encoding a protein which interacts with *Agrobacterium* VirD2 is operably linked to a promoter which directs expression of the VirD2 interacting protein in the host cell. The host cell can include any eukaryotic cell, such as insect, fungal, plant, or animal cell. Preferably, the host cell is a plant cell. Even more preferably, the plant cell is from a monocotyledonous plant species. Host cells made increasingly susceptible to *Agrobacterium* infection are thus better transformed via *Agrobacterium*-mediated gene transfer.

In another aspect of the invention, there is provided a method of improving *Agrobacterium*-mediated gene transfer. The method comprises the steps of: (1) introducing into host cell, a nucleotide sequence encoding VIP1 or VIP1-like protein operably linked to a promoter which directs expression of the nucleotide sequence encoding the VIP1 or VIP1-like protein in the host cell, and (2) transforming the host cell with an *Agrobacterium* transformation vector. Preferably, the *Agrobacterium* transformation vector comprises the *Agrobacterium* Vir region and also comprises a gene of interest positioned between the right and left borders sequences of *Agrobacterium* T-DNA. The host cell can include any eukaryotic cell, such as insect, fungal, plant, or animal cell. Preferably, the host cell is a plant cell. Even more preferably, the plant cell is from a monocotyledonous plant species. The host cell may be transformed with the *Agrobacterium* transformation vector simultaneously with the nucleotide sequence encoding a VIP1 or VIP1-like protein or else following transformation of the host cell with the nucleotide sequence encoding a VIP1 or VIP1-like protein.

In another aspect of the invention, a method of improving *Agrobacterium*-mediated gene transfer comprises the steps of: (1) introducing into a host cell, a nucleotide sequence encoding a protein which interacts with *Agrobacterium* VirD2 and which nucleotide sequence is operably linked to a promoter which directs expression of the VirD2-interacting protein in the host cell, and (2) transforming the host cell with an *Agrobacterium* transformation vector. Preferably, the Agrobacterium transformation vector comprises the Agrobacterium Vir region and also comprises a gene of interest positioned between the right and left borders sequences of Agrobacterium T-DNA. The host cell can include any eukaryotic cell, such as insect, fungal, plant, or animal cell. Preferably, the host cell is a plant cell. Even more preferably, the plant cell is from a monocotyledonous plant species.

In another aspect of the invention, there are provided chimeric genes and expression vectors which, upon introduction into a plant cell, enable the plant cell to become more susceptible to Agrobacterium infection and thus better transformed via Agrobacterium-mediated gene transfer. A subject chimeric gene comprises in the 5' to 3' direction, a promoter which functions in a plant cell operably linked to an open reading frame (ORF) of a VIP1 or VIP1-like gene. In a preferred embodiment, the chimeric gene further comprises a 3' regulatory region which functions in a plant cell, operably linked to the 3' end of the VIP1 or VIP1-like ORF. A subject expression vector comprises such a chimeric gene, i.e., a promoter which functions in a plant cell operably linked to an open reading frame (ORF) of a VIP1 or VIP1-like gene. In a preferred embodiment, within the expression vector the ORF is further operably linked to a 3' regulatory sequence which functions in a plant cell.

Transgenic plant cells and plants regenerated therefrom which overexpress a VIP1 or VIP1-like gene are also provided. In addition, the present invention provides transgenic plant cells and plants regenerated therefrom which overexpress a VIP1 or VIP1-like gene and which express or overexpress an additional gene of interest introduced into the VIP transgenic plant cell via Agrobacterium-mediated transformation. The gene of interest can be a native or foreign gene with respect to the plant cell.

Propagation material from transgenic plants transformed with a VIP1 or VIP1-like gene is also provided. Examples include pollen, ovum, seeds, tubers, roots and cuttings. In addition, progeny and cut flowers from such transgenic plants are also provided.

Host cells which express a VIP1 or VIP1-like transgene are also provided. In addition to plant cells, such host cells may include e.g., insect, animal, or fungal cells.

BRIEF DESCRIPTION OF THE DRAWINGS

FIGS. 5A and 5B show the nucleotide sequence (SEQ ID NO:1) for VIP1 cDNA along with the corresponding amino acid sequence (SEQ ID NO:2).

DETAILED DESCRIPTION OF THE INVENTION

Figure 1A:
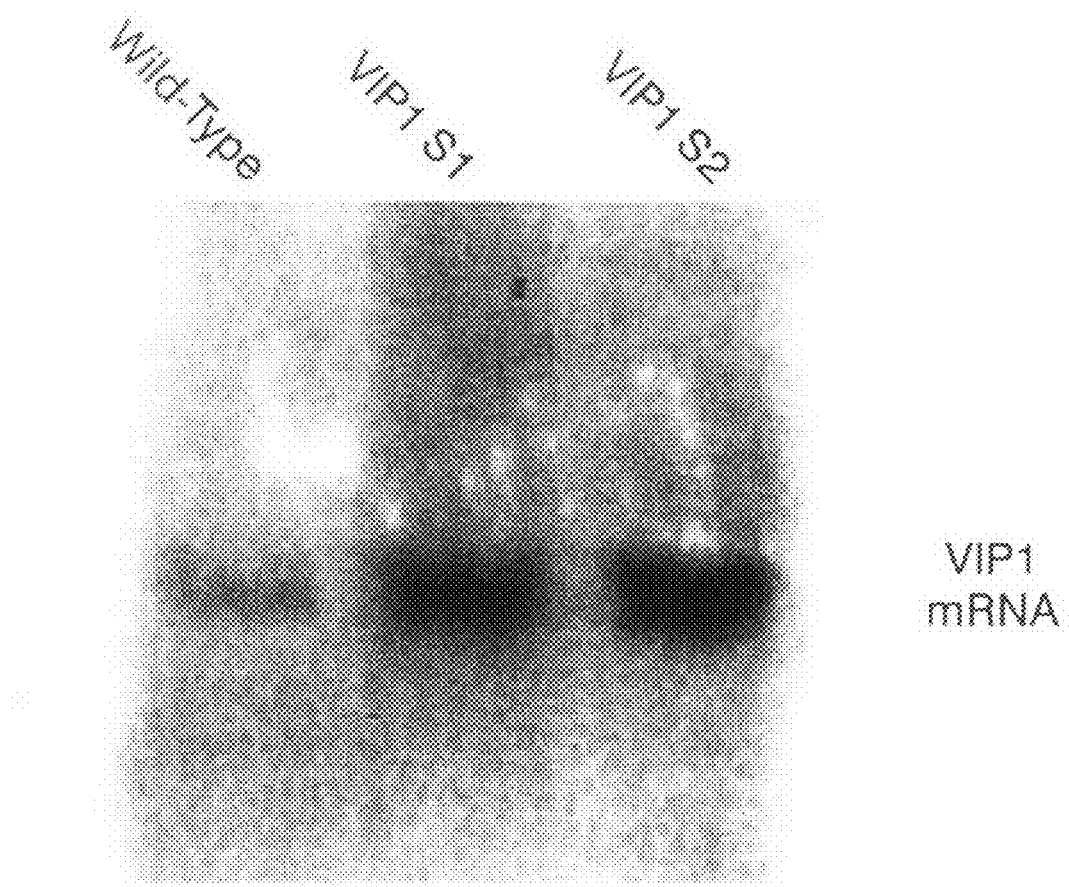
FIG. 1A is a Northern blot analysis of VIP1 expression in wild-type and VIP1 plants. VIP1 S1 and VIP1 S2 represent two independent VIP1 transgenic plant lines.

In accordance with the present invention, it has been discovered that a recently described protein in Arabidopsis, designated VIP1 (VirE2-interacting protein 1)(18) is useful in increasing susceptibility of a host cell to Agrobacterium infection. The present invention therefore provides compositions and methods for expressing VIP1 and homologous proteins from other plant species, hereinafter designated "VIP1-like proteins". The compositions and methods described herein are especially useful in improving Agrobacterium-mediated gene transfer in plant cells.

Thus, in a first embodiment of the invention, there is provided a method of increasing susceptibility of a host cell to Agrobacterium infection. The method comprises the steps of introducing into a host cell, a nucleotide sequence encoding VIP1 or VIP1-like protein, operably linked to a promoter which directs expression of the nucleotide sequence encoding VIP1 or VIP1-like protein in the host cell. The host cell can include any eukaryotic cell, such as an insect, fungal, plant, or animal cell. Preferably, the host cell is a plant cell. Host cells made increasingly susceptible to Agrobacterium infection are thus better transformed via Agrobacterium-mediated gene transfer.

In addition to nucleotide sequences encoding Arabidopsis VIP1, sequences encoding other VIP1-like proteins, herein referred to as "VIP1-like genes or VIP1-like coding sequences" may be employed such as that from Lycopersicon esculentum (tomato), Paulwnia kawakamii, Oryza sativum (rice), and Nicotiana tabacum (tobacco), as well as from other plant species. The coding sequence for the Arabidopsis VIP1 gene is provided in FIG. 5 and is also available on the public databases as DDBJ/EMBL/GenBank accession Nos. AF225983 for the cDNA and AC009526 for the genomic sequence containing the VIP1 gene. Amino acid sequences for VIP-like proteins from other plants may also be obtained from the public genetic databases. For example, a VIP1-like protein from Lycopersicon esculentum is published as NCBI Accession No. CAA52015; a VIP1-like protein from Paulownia kaivakamii is published as NCBI Accession No.

AAC04862; a VIP1-like protein from *Oryza sativum* is published as NCBI Accession No. AAC49832; and a VIP1-like protein from *Nicotiana tobacum* is published as NCBI Accession No. BAA97100.

In an alternative embodiment, a method of increasing susceptibility of a host cell to *Agrobacterium* infection comprises the steps of introducing into a host cell, a nucleotide sequence encoding a protein that interacts with the *Agrobacterium* protein VirD2. Preferably, the nucleotide sequence encoding a protein which interacts with *Agrobacterium* VirD2 is operably linked to a promoter which directs expression of the VirD2 interacting protein in the host cell. Examples of proteins which interact with *Agrobacterium* VirD2 include but are not limited to Roca, roc4, cypa (see Deng, W. et al., 1998 "*Agrobacterium* VirD2 protein interacts with plant host cyclophilins" *Proc. Natl. Acad Sci. USA* 95:7040-7045) and atKAPa (see Ballas, N. and Citovsky, V., 1997 "Nuclear localization signal binding protein from *Arabidopsis* mediates nuclear import of *Agrobacterium* VirD2 protein" *Proc. Natl. Acad. Sci. USA* 94:10723-10728.) The host cell can include any eukaryotic cell, such as insect, fungal, plant, or animal cell. Preferably, the host cell is a plant cell. Even more preferably, the plant cell is from a monocotyledonous plant species. Host cells made increasingly susceptible to *Agrobacterium* infection are thus better transformed via *Agrobacterium*-mediated gene transfer.

In another aspect of the invention, there is provided a method of improving *Agrobacterium*-mediated gene transfer. The method comprises the steps of: (1) introducing into a host cell, a nucleotide sequence encoding VIP1 or VIP1-like protein operably linked to a promoter which directs expression of the nucleotide sequence encoding VIP1 or VIP1-like protein in the host cell, and (2) transforming the host cell with an *Agrobacterium* transformation vector. The host cell may be transformed with the *Agrobacterium* transformation vector simultaneously with the VIP1 gene or following transformation of the host cell with a VIP1 or VIP1-like gene. Preferably, the *Agrobacterium* transformation vector comprises the *Agrobacterium* Vir region and the left and right border sequences of T-DNA. In another preferred embodiment, a gene of interest is positioned between the right and left borders of the *Agrobacterium* T-DNA for transfer into the host cell. In accordance with the present invention, transfer of the gene of interest is facilitated due to the host cell expressing a VIP1 or VIP1-like gene. The host cell can include any eukaryotic cell, such as bacterial, insect, fungal, plant, or animal cells. Preferably, the host cell is a plant cell. Even more preferably, the host cell is a monocot plant cell.

In still another aspect of the invention, a method of improving *Agrobacterium*-mediated gene transfer comprises the steps of: (1) introducing into a host cell, a nucleotide sequence encoding a protein which interacts with *Agrobacterium* VirD2 and which nucleotide sequence is operably linked to a promoter which directs expression of the VirD2-interacting protein in the host cell, and (2) transforming the host cell with an *Agrobacterium* transformation vector. Preferably, the *Agrobacterium* transformation vector comprises the *Agrobacterium* Vir region and also comprises a gene of interest (e.g., a transgene) positioned between the right and left borders sequences of *Agrobacterium* T-DNA. The host cell can include any eukaryotic cell, such as insect, fungal, plant, or animal cell. Preferably, the host cell is a plant cell. Even more preferably, the plant cell is from a monocotyledonous plant species.

As used herein, "a gene of interest" may be any gene desired to be introduced into a host cell. Thus, a gene of interest may either be heterologous, i.e., foreign to the genome of the host cell or native to the host cell. There are of course, a myriad of available genes of interest which may be used in the compositions and methods of the present invention. For example, a gene of interest may encode a disease resistance gene, an insect resistance gene, a stress tolerance gene or a gene encoding a structural protein or an enzyme.

VIP1 and VIP1-like coding sequences and genomic clones may be obtained by screening a cDNA or genomic library with an appropriate probe. For example, a genomic clone or cDNA for a VIP1-like gene may be obtained by screening a genomic library with the *Arabidopsis* VIP1 gene (cDNA or genomic) or fragment thereof An oligonucleotide comprising sequence from the VIP1 cDNA may also serve as probe. For example, oligonucleotide probes corresponding to a conserved stretch of basic amino acids abutting a heptad leucine repeat (leucine zipper) in the *Arabidopsis, Lycopersicon, Paulownia*, and *Nicotiana* VIP1-like genes (see FIG. 2 of reference 18, incorporated by reference herein as if fully set forth) may be designed and used to isolate other VIP1-like genes by hybridising to a cDNA or genomic library. By "hybridizing", it is meant that such nucleic acid molecules hybridize under conventional hybridization conditions, such as described by, e.g., Sambrook et al(1989) *Molecular Cloning; A Laboratory Manual*, $2^{nd}$ Edition, Cold Spring Harbor Press, Cold Spring Harbor, N.Y.

Nucleic acid molecules hybridizing to VIP1 can be isolated, e.g., from cDNA or genomic libraries by techniques well known in the art. Methods considered useful in obtaining DNA sequences corresponding to a VIP1 gene or VIP1-like gene by screening a cDNA or genomic library, are provided in Sambrook et al. (1989), for example, or any of the myriad of laboratory manuals on recombinant DNA technology that are widely available.

A VIP1 or VIP1-like gene for use in the present invention is not necessarily isolated from a gene library but may be generated in any manner, including for example, chemical synthesis, DNA replication, transcription, and reverse transcription. For example, the coding region of a VIP1 or VIP1-like gene can be amplified using PCR technology. In addition, as originally performed in identifying the *Arabidopsis* VIP1 gene, the yeast two-hybrid screen system (Fields and Song, 1989, Hollenberg et al. 1995) may also be employed to isolate a VIP1-like gene using a plant cDNA library and *Agrobacterium* VirE2 as bait (18).

The general techniques used in the subject invention, especially in preparing and probing a cDNA or genomic library, sequencing isolated clones, performing deletion analysis, constructing expression vectors, transforming cells and growing cells and the like are known in the art and laboratory manuals describing such techniques are widely available. See e.g. Sambrook et al. $2^{nd}$ Ed., (1989).

In order to express VIP1 or VIP1-like protein in a host cell, an open reading frame (ORF) for a VIP1 or VIP1-like gene is preferably operably lined to one or more regulatory elements which function to control expression of the VIP1 or VIP1-like gene in the host cell. Examples of regulatory elements which may be used to drive expression of VIP1 or VIP1-like genes in eukaryotic cells include the AOX1 or GAL1 promoter in yeast or the CMV promoter, SV40 promoter, or RSV-promoter in mammalian or other animal cells.

In accordance with the present invention, the VIP1 or VIP1-like coding sequence may correspond to a cDNA or genomic sequence. When a genomic VIP1 or VIP1-like gene is used, the gene may be altered, if desired, to remove or add one or more introns. In addition, signal sequences may be removed and/or added to the genomic sequence. Signal sequences and/or intron(s) may also be added to a VIP1 or VIP1-like cDNA. Nucleotide sequences for a VIP1 or VIP1-like gene, which may include one or more introns, may be operably linked to a promoter from the same VIP1 or VIP1-like gene or to a promoter from another VIP1 gene. Alternatively, the VIP1 or VIP1-like nucleotide sequences may be operably linked to a promoter which functions in plant cells but which is unrelated to a VIP1 or VIP1-like gene. When the VIP1 or VIP1-like ORF is operably linked to a promoter other than that naturally located 5' upstream from the VIP1 or VIP1-like coding sequence, such a nucleotide sequence may be referred to as a chimeric gene or a chimeric gene construct.

A 5' regulatory region (including a promoter) of a VIP1 or VIP1-like gene can be derived from restriction endonuclease digestion of an isolated VIP1 or like genomic clone. Thus, for example the known nucleotide or amino acid sequence for a VIP1 or VIP1-like gene may be aligned to the nucleic acid or deduced amino acid sequence of an isolated VIP1 or VIP1-like genomic clone and the 5' regulatory sequence (i.e. sequence upstream from the translational start codon of the coding region), coding sequence, and 3' regulatory sequence (i.e., sequence downstream from the translational stop codon of the coding region) of the isolated VIP1 or VIP1-like gene located. The 5' or 3' regulatory region can be excised using convenient restriction enzymes. In vitro mutagenesis can be used to introduce convenient restriction sites. There are various commercially available kits particularly suited for this application such as the T7-Gen in vitro mutagenesis kit (USB, Cleveland, Ohio) and the QuickChange Sire Directed Mutagenesis Kit (Stratagene, San Diego, Calif.). Alternatively, PCR primers can be defined to allow direct amplification a VIP1 or VIP1-like gene, including the promoter, coding sequence, and 3' regulatory sequence.

Examples of promoters which function constitutively in plant cells and which may be operably linked to a VIP1 or VIP1-like gene include the cauliflower mosaic virus (CaMV) 35S promoter, nopaline synthase (nos) promoter, Alfalfa Mosaic Virus (AMV) promoter, and enhanced mannopine synthase promoter (MAC promoter). Other constitutive promoters for use in plant cells include the polyubiquitin promoter, and the actin promoter for ubiquitin expression. These promoters are well characterized and widely available. Examples of inducible promoters which may be used to control expression of an VIP gene include heat shock promoters, a nitrate-inducible promoter derived from the spinach nitrate reductase gene (Back et al. 1991 *Plant Mol. Biol.* 17:9), hormone inducible sequences (e.g., Yamagushi-Shinzaki, E. et al. 1990 *Plant Mol. Biol.* 15:905, Kares et al (1990) *Plant Mol. Biol.* 15:225) and light inducible promoters such as the small subunit of RuBP carboxylase and LHCP gene families. Another example of an inducible promoter is a tetracycline-inducible promoter (Gatz et al. 1992 *Plant .J.* 2:397).

Tissue specific and developmentally regulated promoters may also be used to control and regulate expression of a VIP1 or like gene in a plant cell. Examples include pollen-specific (Albani et al. 1991 *Plant Mol. Biol.* 16:501; Twell, et al., 1991 *Genes Dev.* 5:496; Hamilton D. et al., 1992 *Plant Mol. Biol.* 18:211), flower-specific (van der Meer et al. 1990 *Plant Mol. Biol.* 15:95, root specific (Depater, B. S. et al., 1992 *Plant Mol. Biol.* 18:161; Vanderzaal, e.., et al. 1991 *Plant Mol. Biol.* 16:983; Oppenheimer, D. G., et al., 1988 *Gene* 63:87) and seed-specific promoters (Bustos, M. M., et al., 1991 *EMBO J.* 10:1469; Stayton,M., et al., 1991 *Aust. J. Plant Physiol.* 18:507). Meristem-specific promoters, which are well known in the art (e.g. as described in U.S. Pat. No. 5,898,096), may also be used in order to regulate expression of a VIP1 or VIP1-like protein in the meristematic regions of a plant.

Preferably, the nucleotide sequence encoding a VIP1 gene or VIP1-like gene is contained within a vector that can replicate within the host cell and may also be referred to as a genetic construct. Preferably, the vector is an expression vector. The term "vector" is used broadly herein and is intended to encompass any medium which includes nucleic acid and which can be used to transform a host cell. An "expression vector" is a construct that can be used to transform a selected host cell and provides for expression of a coding sequence in a selected host. Expression vectors can thus encompass many different cloning vectors such as plasmids, phagemids, phage, cosmids, yeast artificial chromosomes, linear DNA vectors, binary vectors, integrating vectors, and *Agrobacterium* plant transformation vectors. To provide regulated expression of a VIP1 or VIP1-like gene in a plant, plants are transformed with a nucleic acid sequence comprising a promoter which functions in plants, operably linked to a cDNA or genomic VIP1 or VIP1-like sequence. "Operably linked" as used herein refers to a juxtaposition wherein the components so described are in a relationship permitting them to function in their intended manner. Thus, for example, a VIP1 or VIP1-like gene operably linked to a promoter and/or 3' regulatory sequence means that the promoter and terminator sequences function to regulate transcription. Preferably, the VIP1 or VIP1-like gene also comprises a 3' regulatory sequence. There are many different 3' regulatory sequences comprising transcription termination signals and in some cases, polyadenylation sites, which may be operably linked to the 3' end of the coding sequence of a VIP1 or VIP1-like gene. Examples include the nopaline synthase termination signal or CaMV 35S. Additional regulatory elements may include transcriptional as well as translational enhancers. A plant translational enhancer often used is the Tobacco Mosaic Virus omega sequence.

As used herein, the term 'plant' includes reference to whole plants, plant organs (such as leaves, roots, stems, etc.), seeds and plant cells and progeny of same. 'Plant cell' as used herein includes protoplasts, suspension cultures, embryos, meristematic regions, callus tissue, leaves, explants, seeds, roots, shoots, gametophytes, sporophytes, pollen, and microspores. Plants that can be used in the methods of the invention include all plants which belong to the superfamily Viridiplantae, including both monocotyledonous and dicotyledonous plants. Particularly preferred plants are monocotyledonous plants which, as a group, are notoriously recalcitrant to *Agrobacterium*-mediated transformation. Examples of monocot plants which are particularly preferred for use in the present invention include but are not limited to cereal crops such as maize, rice, barley, wheat, rye, and oats. Woody plant species such as shrubs and trees are also particularly preferred. However, any plant species, (either monocot or dicot and including crop plants and ornamentals, herbaceous or woody), may be used in and can be benefited by, the methods of the present invention as it has been discovered that *Agrobacterium*-mediated transformation of tobacco, one of the natural hosts of *Agrobacterium*, does not even occur at its maximal possible efficiency and is improved by increasing the intracellular levels of VIP1.

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid, or alternatively, may be integrated into the host genome. Methods for the introduction of foreign DNA into host cells are well known and include e.g., electroporation, lithium acetate transformation, spheroplasting, and the like.

The vectors used in the method of the invention may contain further functional elements, for example "left border" and "right border"-sequences of the T-DNA of *Agrobacterium* which are required for genetic transformation. Advantageously, vectors of the invention comprise a selectable and/or scorable marker. Selectable marker genes useful for the selection of transformed plant cells, callus, plant tissue and plants are well known to those skilled in the art. For example, antimetabolite resistance provides the basis of selection for: the dhfr gene, which confers resistance to methotrexate (Reiss, Plant Physiol. (Life Sci. Adv.) 13 (1994), 143-149); the npt gene, which confers resistance to the aminoglycosides neomycin, kanamycin and paromomycin (Herrera-Estrella, EMBO J. 2 (1983), 987-995); and hpt, which confers resistance to hygromycin (Marsh, Gene 32 (1984), 481-485). Useful scorable markers are also known to those skilled in the art and are commercially available. For example, the genes encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907) may be used.

The VIP1 or VIP1-like gene, preferably contained within an expression vector, may be introduced into a plant or plant cell via any of the well known methods of gene transfer in plants. Methods of gene transfer in plants are well known (see e.g., Gelvin 1998 *Curreni Opin. Biotech.* 9:227) and include, for example, transformation of plant cells or tissues with T-DNA using *Agrobacterium tumefaciens* or *Agrobacterium rhizogenes* as described essentially by An et al. (*EMBO J* 4:277-284, 1985), Herrera-Estrella et al. (*Nature* 303: 209-213, 1983a; *EMBO J.* 2: 987-995, 1983b; In: Plant Genetic Engineering, Cambridge University Press, N.Y., pp 63-93, 1985), Bechtold el al., (*C.R. Acad. Sci. (Paris* 316: 1194-1199, 1993) or Clough et al (*Plant J.* 16: 735-743, 1998); protoplast fusion, micoinjection (Potrykus and Spangenberg (eds.), Gene Transfer To Plants. Springer Verlag, Berlin, N.Y. 1995); electroporation (Fromm et al., *Proc. Natl. Acad. Sci. USA* 82:5824-5828, 1985); biolistic methods like particle bombardment, pollen-mediated transformation, plant virus-mediated transformation, liposome-mediated transformation, transformation using wounded or enzyme-degraded immature embryos, or wounded or enzyme-degraded embryogenic callus and other methods known in the art. Methods for plant transformation using biolistic methods are well known to the person skilled in the art; see, e.g., Wan, Plant Physiol. 104 (1994), 37-48; Vasil, Bio/Technology 11 (1993), 1553-1558 and Christou (1996) Trends in Plant Science 1, 423-431.

It is well established that different plant species and different transformation protocols require different *Agrobacterium* strains with different genomic backgrounds and binary plasmids. Thus, in a given scenario, where the transformation conditions are dictated by a well-established transformation protocol (i.e. the use of a specific *Agrobacterium* strain, a specific tissue, tissue culture conditions and infection methods), the methods and compositions of the present invention are useful for increasing the transformation efficiency of such specific protocol. It is not unusual for it to take a number of years to establish a reliable and reproducible transformation protocol for difficult-to-transform species. Genetically increasing the susceptibility of a given species to an existing transformation protocol using the subject methodologies and/or compositions is therefore an important aspect of the present invention. Thus, the subject VIP1 or VIP1-like compositions and methods may be used in conjunction with any existing or future-developed transformation protocol, for any given plants species, and any given *Agrobacterium* strain, in order to further enhance and improve the transformation efficiency.

Current systems for monocot genetic transformation include the use of protoplasts and biolistics (see e.g. Rasco-Gaunt S, Riley A, Cannell M, Barcelo P, Lazzeri P. A., (2001) "Procedures allowing the transformation of a range of European elite wheat (*Triticum aestivum L.*) varieties via particle bombardment." *J Exp Bot* 52(357): 865-74; and Datta K, Datta S. K., (1999) "Transformation of rice via PEG-mediated DNA uptake into protoplasts." *Methods Mol Biol.* 111: 335-347.

In general, these systems have very low efficiency and very poor reproducibility (reviewed in Smith R H. and Hood E. H. (1995). "*Agrobacterium tumefaciens* of monocotyledons." *Crop Sci.* 35: 301-308). In recent years, it has been shown that *Agrobacterium* can transform a wide range of monocotyledons species and varieties, thus making it the choice for genetic engineering of many crop species. Id. Nevertheless, *Agrobacterium*-mediated genetic transformation of many monocotyledons still remains laborious and relatively inefficient. Amoah B K, Wu H, Sparks C, Jones H. D.,(2001) "Factors influencing *Agrobacterium*-mediated transient expression of uidA in wheat inflorescence tissue." *J Exp Bot.* 52:1135-1142; Zhao Z Y, Cai T, Tagliani L, Miller M, Wang N, Pang H, Rudert M, Schroeder S, Hondred D, Seltzer J, Pierce D.(2000) "*Agrobacterium*-mediated sorghum transformation." *Plant Mol Biol.* 44:789-98; Clemente, T., LaVallee, B., Howe, A., Ward, D., Rozman, R., Hunter, P., Broyles, D., Kasten, D., Hinchee, M. (2000) "Progeny analysis of glyphosate selected transgenic soybeans derived from *Agrobacterium*-mediated transformation." *Crop Sci.* 40: 797-803.

Other means for introducing recombinant DNA into plant tissue or cells include, but are not limited to, transformation using $CaCl_2$ and variations thereof, in particular the method described by Hanahan (*J. Mol. Biol.* 166, 557-560, 1983), direct DNA uptake into protoplasts (Krens et al, *Nature* 296: 72-74, 1982; Paszkowski et al, *EMBO J.* 3:2717-2722, 1984), PEG-mediated uptake to protoplasts (Armstrong et al, *Plant Cell Reports* 9: 335-339, 1990) and the leaf disk transformation-regeneration procedure as described by Horsch et al. *Science*, 227; 1229-1231 (1985).

As used herein, 'transgenic plant' includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a vector. 'Transgenic' is used herein to include any cell, cell line, callus, tissue, plant part or plant, the genotype of which has been altered by the presence of the heterologous nucleic acid including those transgenics initially so altered as well as those created by sexual crosses or asexual propagation from the initial transgenic. Thus, the present invention further provides a transgenic plant which overexpresses a VIP1 or VIP1-like gene. The VIP1-like gene may be foreign to the transgenic plant, i.e., not naturally found within the genome of the transgenic plant. The VIP1-like gene may also be native to the transgenic plant, i.e., normally found within the genome of the transgenic plant. Since VIP1 and VIP1-like genes encode cellular proteins normally expressed in plant cells, the VIP1 and VIP1-like genes can be said to be overexpressed in a subject transgenic plant.

Plant transformation vectors can be derived by modifying the natural gene transfer system of *Agrobacterium tumefa*-

*ciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Suitable strains of *Agrobacterium tumefaciens* and vectors as well as transformation of Agrobacteria and appropriate growth and selection media are well known to those skilled in the art and are described in the prior art e.g., Koncz et al. (1986), *Mol. Gen. Genet.* 204: 383-396; Deblaere et al. (1985), *Nucl. Acid Res.* 13: 4777; Bevan et al. (1984) *Nucleic. Acid Res.* 12: 8711; Koncz, Proc. Natl. Acad. Sci. USA 86 (1989), 8467-8471; Klett et al. (1987) *Annu. Rev. Plant Physiol.* 38; 467; Koncz, Plant Mol. Biol. 20 (1992), 963-976; Koncz, "Specialized vectors for gene tagging and expression studies" In: *Plant Molecular Biology Manual* Vol 2, Gelvin and Schilperoort (Eds.), Dordrecht, The Netherlands, Kluwer Academic Publ. (1994); An et al. (1985) *EMBO J.* 4: 277-287. Such transformation vectors include binary-, super-binary, cointegrate- and Ri-derived vectors and T-DNA carrying vectors. Although the use of *Agrobacterium* tumefaciens is preferred in the method of the invention, other *Agrobacterium* species, such as *Agrobacterium rhizogenes*, may be used.

For example, surface-sterilized leaf disks and other susceptible tissues may be inoculated with the "disarmed" *A. tumefaciens* containing foreign-DNA, cultured for a number of days, and then transferred to antibiotic-containing medium. Transformed shoots may then be selected after rooting in medium containing the appropriate antibiotic, and transferred to soil. Transgenic plants may be pollinated and seeds from these plants are collected and grown on antibiotic medium.

Expression of a VIP1 or VIP1-like gene in developing seeds, young seedlings and mature plants can be monitored by immunological, histochemical, mRNA expression or activity assays. For assaying expression of VIP1 or VIP1-like gene, Northern and Western analysis may be performed.

Thus, following the methods described herein, the present invention further provides a transgenic plant or progeny thereof which overexpresses a VIP1 or VIP1-like gene. In addition, following the methods described herein, the present invention provides a transgenic plant or progeny thereof which overexpress a VIP1 or VIP1-like gene and which expresses or overexpresses an additional gene of interest introduced into the VIP transgenic plant via *Agrobacterium*-mediated transformation. The gene of interest can be a native or foreign gene with respect to the plant cell and may be introduced subsequently to, or simultaneously with, a VIP1 or VIP1-like gene.

Plant cells may be transformed with a VIP1 or VIP1-like gene construct by any of the plant transformation methods described above. The transformed plant cell, usually in the form of a callus culture, leaf disk, or explant may be regenerated into a complete transgenic plant by methods well-known to one of ordinary skill in the art (e.g., Horsh et al., 1985). Since progeny of the subject transformed plants inherit the VIP1 or VIP1-like gene, propagation material such as e.g., pollen, ovum, seeds, tubers or cuttings from transformed plants may be used to maintain the transgenic trait in the transformed line. The present invention also encompasses cut flowers, especially with respect to those from regenerated ornamental plants transformed with a VIP1 or VIP1-like gene.

The following examples further illustrate the invention and are not intended in any way to limit the invention.

EXAMPLE 1

Materials and Methods

Plasmid construction. For generation of VIP1 transgenic plants, the *Arabidopsis* VIP1 ORF[18] was first inserted as a polymerase chain reaction (PCR)-amplified SalI fragment into a plant expression vector, pCd, containing the 35S promoter of cauliflower mosaic virus, tobacco mosaic virus translational enhancer[30], and the nopaline synthase polyA signal. Then, the entire expression cassette was subcloned as a BamHI-XbaI fragment into the binary vector pBIN19, carrying a kanamycin selection marker, to produce pBIN19-VIP1.

Because the VIP1 plants are already resistant to kanamycin, to select for their genetic transformation by *Agrobacterium* and to characterize the subsequent expression of the transgenes, it was necessary to use a binary vector with a different antibiotic resistance. Thus, the plasmid pBIG-HYG-GUS[25] was chosen, which carries on its T-DNA two reporter genes: the hpt gene encoding hygromycin resistance, and an intron-containing uidA gene encoding β-glucuronidase (GUS).

Generation of VIP1 tobacco plants. The binary vector pBIN19/VIP1 was introduced into the disarmed *Agrobacterium* strain EHA105 which was then used to transform tobacco plants (*Nicotiana tabacum* cv. Turk) as described[26]. Transgenic tobacco plants expressing VIP1 were selected on a kanamycin-containing medium and maintained and propagated at sterile conditions on an MS basal medium[31] with no exogenous growth regulators. Plants were then transferred to soil in a greenhouse, allowed to set seed, and the transgenic progeny was selected by germinating the seeds on MS agar in the presence of kanamycin.

Assays for *Agrobacterium*-induced genetic transformation. For stable genetic transformation assays, 9 mm disks were excised from leaves of one month-old wild-type plants or VIP1 plants, submerged in a culture of the *Agrobacterium* strain EHA105 ($A_{600}$=0.1, 0.5, or 1.0 as indicated for each individual experiment) harboring the pBIG-HYG-GUS binary plasmid, and incubated for 30 min at room temperature, followed by co-cultivation for 48 hr at 25° C. on tobacco regeneration medium[26]. The disks were then washed three times in sterile distilled water, blotted dry, and cultured on the regeneration medium in the presence of 50 μg/ml hygromycin to select for transformed shoots and 300 μg/ml carbenicillin, to eliminate *Agrobacterium*. Six weeks later, the developed shoots were photographed and counted. For whole-shoot GUS staining, the shoots were allowed to grow for 2 more weeks, removed from the parental leaf disk, and stained as described for histochemical detection of transient GUS expression (see below).

For transient T-DNA gene expression, the GUS activity within the leaf disks that had been co-cultivated for 48 hr at 25° C. with *Agrobacterium* as described above for shoot regeneration, was analyzed histochemically by staining with the chromogenic substrate X-Gluc[25]. In control experiments, GUS activity was determined in leaf disks microbombarded with pRTL2-GUS[32], followed by incubation for 24 hr at 25° C. to express the transfected DNA. For biolistic delivery, 1 μg of DNA was adsorbed onto 1 μl of 1-μm gold particles according to the instructions of the manufacturer (BioRad, California) and microbombarded into 25-mm target leaf disks at a pressure of 150 psi using a portable Helios gene gun system (Model PDS-1000/He, BioRad, Calif.). All transformations included 10-20 leaf disks per experimental system.

Northern blot analyses of VIP1 plants. Total RNA was isolated from 200 mg of leaf tissue using the TRI-REAGENT™ extraction kit (Molecular Research Center, Inc., Cincinnati, Ohio). To remove contaminating DNA, the isolated total RNA (100 μg) was incubated at 37° C. for 15 min in 20 mM $MgCl_2$, 2 mM DTT with 1.6 units of RNase-free RQ1-DNaseI (Promega, Wis.) in the presence of about 8 units of placental ribonuclease inhibitor (rRNasine®, Promega), and the reaction was terminated with 0.25 volume of DNase-stop mixture (50 mM EDTA, 1.5 M sodium acetate, 1% w/v SDS). Ten micrograms of total RNA per lane were then electrophoresed on an 1.7% formaldehyde-agarose gel and probed with [$^{32}$P]-labeled VIP1 cDNA, followed by autoradiography as described[33]. Ribosomal RNA (rRNA) within the analyzed RNA preparation was detected by ethidium bromide staining of agarose gels and served as an internal control for equal loading of the lanes (FIG. 1B).

EXAMPLE 2

Results

Overexpression of VIP1 in transgenic plants. To examine whether VIP1 may represent one of the limiting cellular factors during *Agrobacterium* infection, transgenic tobacco plants that overexpress the *Arabidopsis* VIP1 cDNA[18] were constructed. A total of fifteen independently-transformed transgenic lines were produced, and two lines, designated VIP1 S1 and VIP1 S2, were analyzed in detail.

Figure 1B:
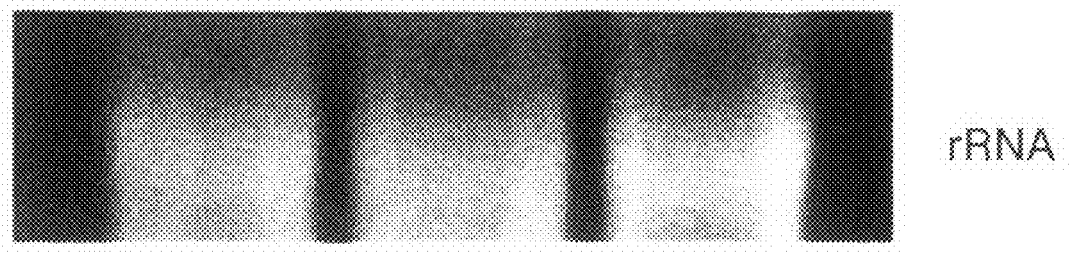
FIG. 1B is a gel photograph showing the amounts of rRNA in each lane Northern blotted as detected by ethidium bromide staining. Lane 1, wild-type plants; lane 2, VIP1 S1 line; lane 3, VIP1 S2 line.

FIG. 1A shows that Northern blot analysis of total RNA obtained from both VIP1 S1 and S2 plants detected high levels of the VIP1 transcript, although the VIP1 mRNA accumulation in the S2 line was slightly higher than that in the S1 line. In contrast, the amount of the endogenous tobacco VIP1 transcript in the wild-type plants was significantly lower indicating that VIP1 does not represent an abundant cellular protein. FIG. 1B confirms that equal loading of all samples occurred in Northern gel as reflected by equal amounts of ribosomal RNA (rRNA) present in all lanes.

Notably, both VIP1 transgenic lines were indistinguishable from the wild-type plants in their overall morphology. Also, no changes in seed viability were observed between the VIP1 and the wild-type plants (data not shown). Thus, overexpression of VIP1 most likely did not interfere with essential plant cellular functions.

Increased susceptibility of VIP1 transgenic plants to *Agrobacterium* infection. The VIP1 transgenic plants were tested for their susceptibility to *Agrobacterium* infection. Three fundamental criteria for the *Agrobacterium*-mediated genetic transformation were used: transient expression of the T-DNA, regeneration of the stably-transformed shoots, and expression of the β-glucuronidase (GUS) reporter enzyme in the regenerated transformed plantlets. To better estimate the effects of VIP1 on the efficiency of infection, three different inocula of *Agrobacterium* were used in each experiment.

Figure 2A:
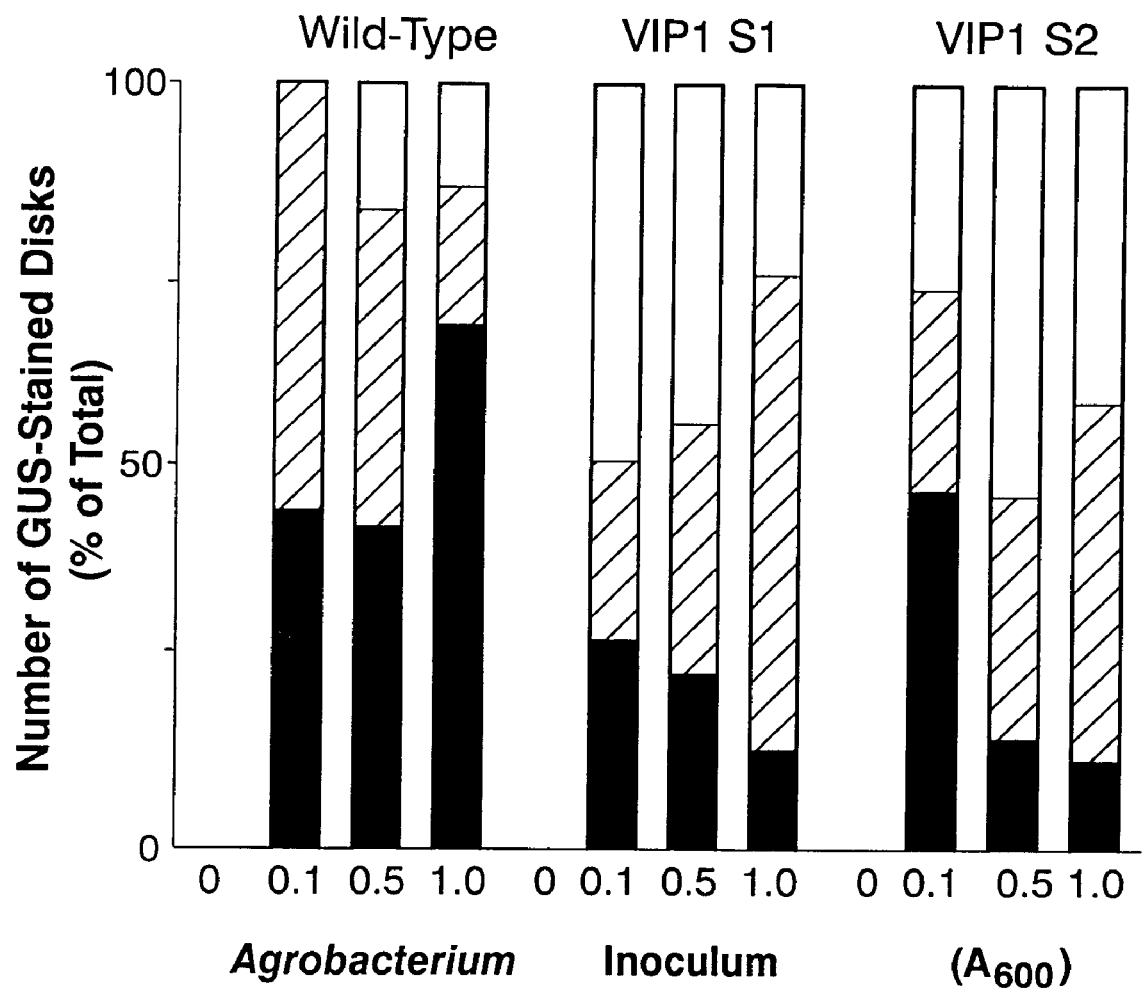
FIG. 2A graphically depicts increased Agrobacterium-mediated genetic transformation of VIP1 S1 and S2 plants and shows quantification of transient T-DNA expression. Black, gray, and white bars indicate the numbers of disks that developed 1-50, 51-99, and 100-150 GUS-stained areas per disk, respectively. Total number of GUS-stained disks for each experimental condition was defined as 100%. All data represent three independent experiments with at least 20 disks per each experimental condition.

Early expression of genes contained on the *Agrobacterium* T-DNA is transient, reaching its maximum approximately 2 days after infection[23, 24] and occurring from the T-DNA molecules that have not yet integrated into the plant genome. To assay transient T-DNA expression, leaf disks derived from the wild-type and VIP1 S1 and S2 lines were inoculated with *Agrobacterium* carrying on its T-DNA a uidA gene encoding the GUS enzyme. The indigo-stained areas, representing GUS activity and thus transient T-DNA expression, on each disk were counted 48 hours after inoculation. The resulting data for each plant line and bacterial inoculum were subdivided into three groups: number of disks that developed 1 to 50, 51 to 99, and 100-150 stained areas per disk. FIG. 2A shows that while in the absence of *Agrobacterium* no GUS staining was observed, co-cultivation of the wild-type leaf disks with the increasing amounts of *Agrobacterium* resulted in the increased number of GUS-stained leaf areas. Specifically, at the lowest bacterial inoculum, approximately 40% of the disks were categorized in the "1 to 50" group, and the rest of the disks exhibited an average of 58 GUS-stained areas per disk. At higher bacterial inocula, a relatively small percentage of the wild-type disks (10-15%) developed an average of 110 and 112 GUS-stained areas per disk for when co-cultivated with *Agrobacterium* cultures of $A_{600}$=0.5 and 1.0, respectively (FIG. 2A). Co-cultivation of the VIP1 S1 and VIP1 S2 leaf disks with *Agrobacterium* resulted in T-DNA expression levels significantly higher than those observed in the wild-type leaf disks. For example, even at the lowest *Agrobacterium* concentration ($A_{600}$=0.1), 49% of the disks from the VIP1 S1 plants and 25% of the disks from the VIP1 S2 plants exhibited an average of 142 and 130 GUS-stained areas per disk, respectively. At higher inocula of $A_{600}$=0.5 and $A_{600}$=1.0, 40% and 24% of the VIP1 S1 plants developed an average of 140 and 143 GUS-stained areas per disk, respectively, and 55% and 42% of the VIP1 S2 plants developed an average of 135 and 138 GUS-stained areas per disk, respectively. Statistical evaluation of the "100 to 150" groups for the $A_{600}$=0.5 and 1.0 inocula using the unpaired two tailed T-test confirmed that the observed differences in T-DNA transient expression between the wild-type plants and both lines of the VIP1 plants were statistically significant (probability >95%). Because the uidA gene contained an intron[25], these results represented the GUS activity directed by the T-DNA after its transfer to the plant rather than its potentially leaky expression within *Agrobacterium*. Importantly, the wild-type and VIP1 plants displayed comparable levels of GUS expression (200-300 GUS-stained areas per disk, data not shown) when the uidA gene was delivered biolistically, indicating that the elevated amounts of VIP1 in the S1 and S2 plants did not non-specifically increase the degree of gene expression in the VIP1-expressing cells.

Figure 3A:
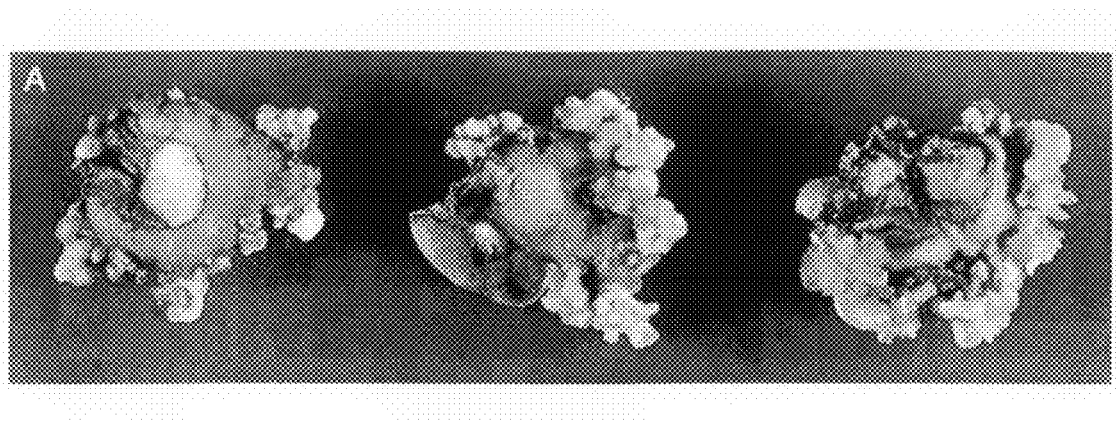
FIGS. 3A through 3C show Agrobacterium-infected disks from the VIP1 S1 line (FIG. 3A), VIP1 S2 line (FIG. 3B), or wild-type plants (FIG. 3C), respectively, grown on hygromycin-containing selective medium. Left to right: disks inoculated with Agrobacterium cultures at $A_{600}$=0.1, 0.5, and 1.0, respectively.
Figure 3B:
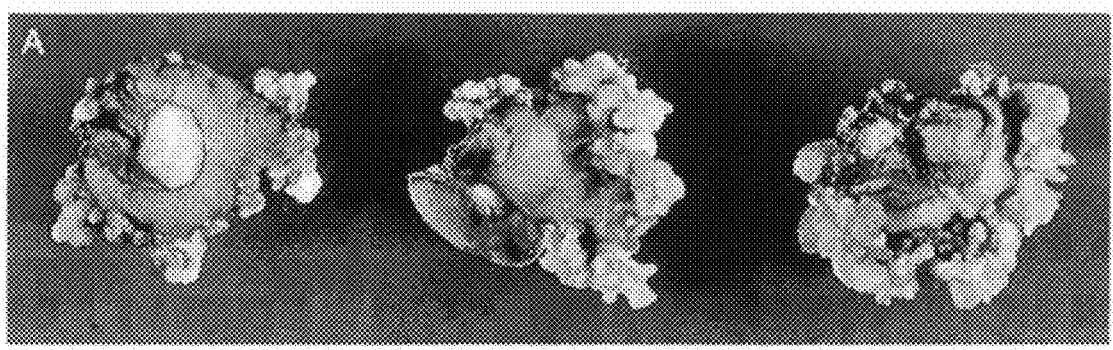
Figure 3C:
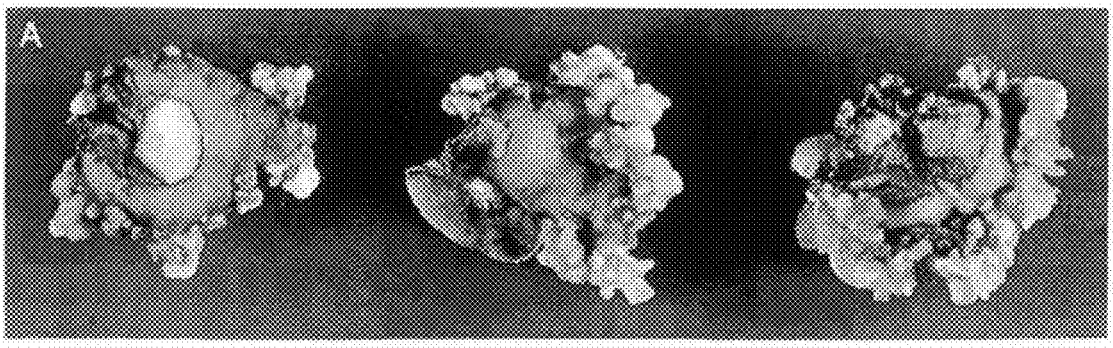
Figure 3D:
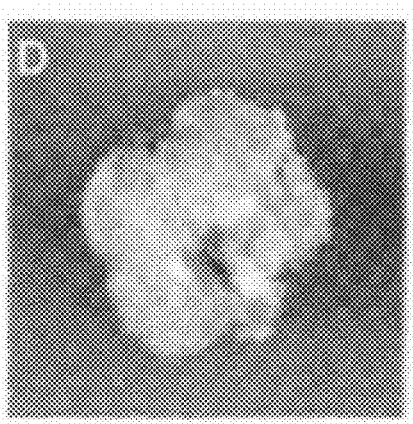
FIGS. 3D-3F show uninfected disks from wild-type plants, VIP1 S1 line, or VIP1 S2 line, respectively, grown on hygromycin-containing selective medium.
Figure 3E:
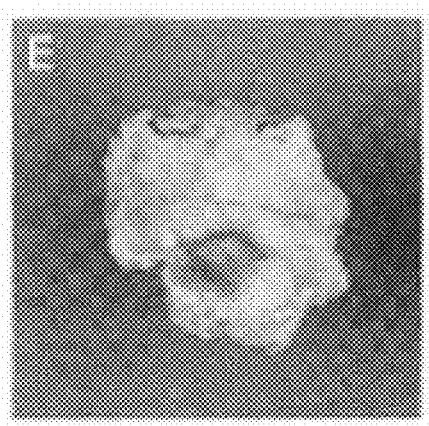
Figure 3F:
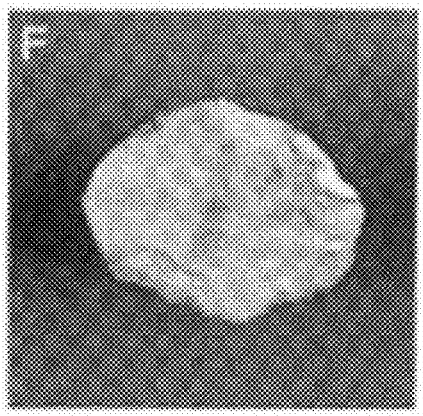
Figure 3G:
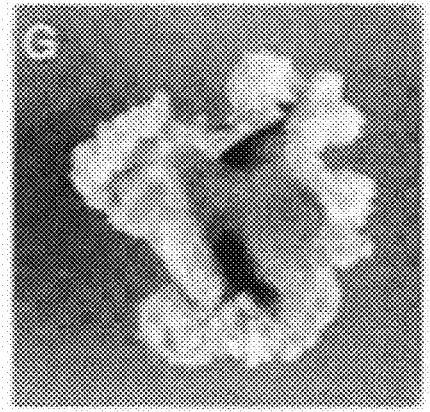
FIG. 3G-3I show uninfected disks from the wild-type plants, VIP1 S1 line, or VIP1 S2 line, respectively, grown in the absence of selection.
Figure 3H:
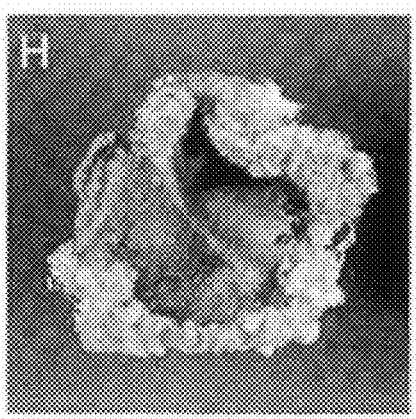
Figure 3I:
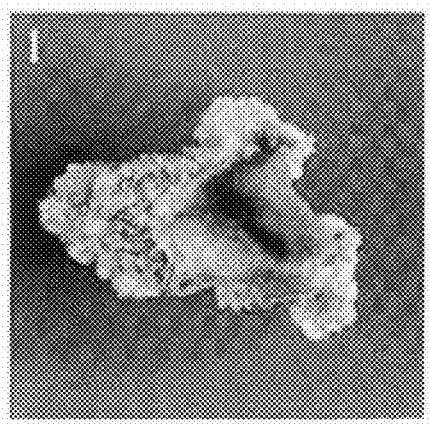

Next, the ability of the VIP1 plants to regenerate transgenic shoots following genetic transformation by *Agrobacterium* carrying two marker genes, hpt and uidA, on its T-DNA was examined. Leaf disks derived from the VIP1 S1 and S2 plant lines and from the wild-type tobacco plants were inoculated with increasing amounts of *Agrobacterium* and cultured on the regeneration medium[26] in the presence of hygromycin to allow regeneration and growth of the transgenic shoots. FIGS. 3A and 3B show that both VIPT plant lines produced a large number of hpt-expressing, hygromycin-resistant shoots (panels A and B). The number of shoots per disk increased with an increase in the *Agrobacterium* inoculum such that, at the highest bacterial concentration used, the entire circumference of the infected disk was virtually saturated with growing transformed shoots. In contrast, the infected leaf disks derived from the wild-type plants regenerated much fewer hygromycin-resistant shoots; although the number of these regenerated shoots also increased with the increasing *Agrobacterium* inoculum (FIG. 3C), it never reached the same high density observed with the VIP1 leaf disks even at the lowest concentration of *Agrobacterium* (compare FIG. 3C to FIGS. 3A and 3B). In control experiments, leaf disks from the wild-type plants (FIG. 3D) and from the VIP1 S1 and VIP1 S2 lines (FIGS. 3E and 3F, respectively) grown on the selective medium but in the absence of *Agrobacterium* infection produced no shoots at all, ruling out a possibility that VIP1 expression rendered the VIP1 plants resistant to hygromycin and enabled them to regenerate untransformed shoots even on the selective medium. Another type of control experiment demonstrated that the regeneration capacity of the wild-type plants (FIG. 3G) in the absence of selection was comparable to that of the VIP1 S1 and VIP1 S2 plants (FIGS. 3H and 3I, respectively), indicating that overexpression of VIP1 in these transgenic lines was not responsible for non-specifically increasing their regeneration potential.

Figure 2B:
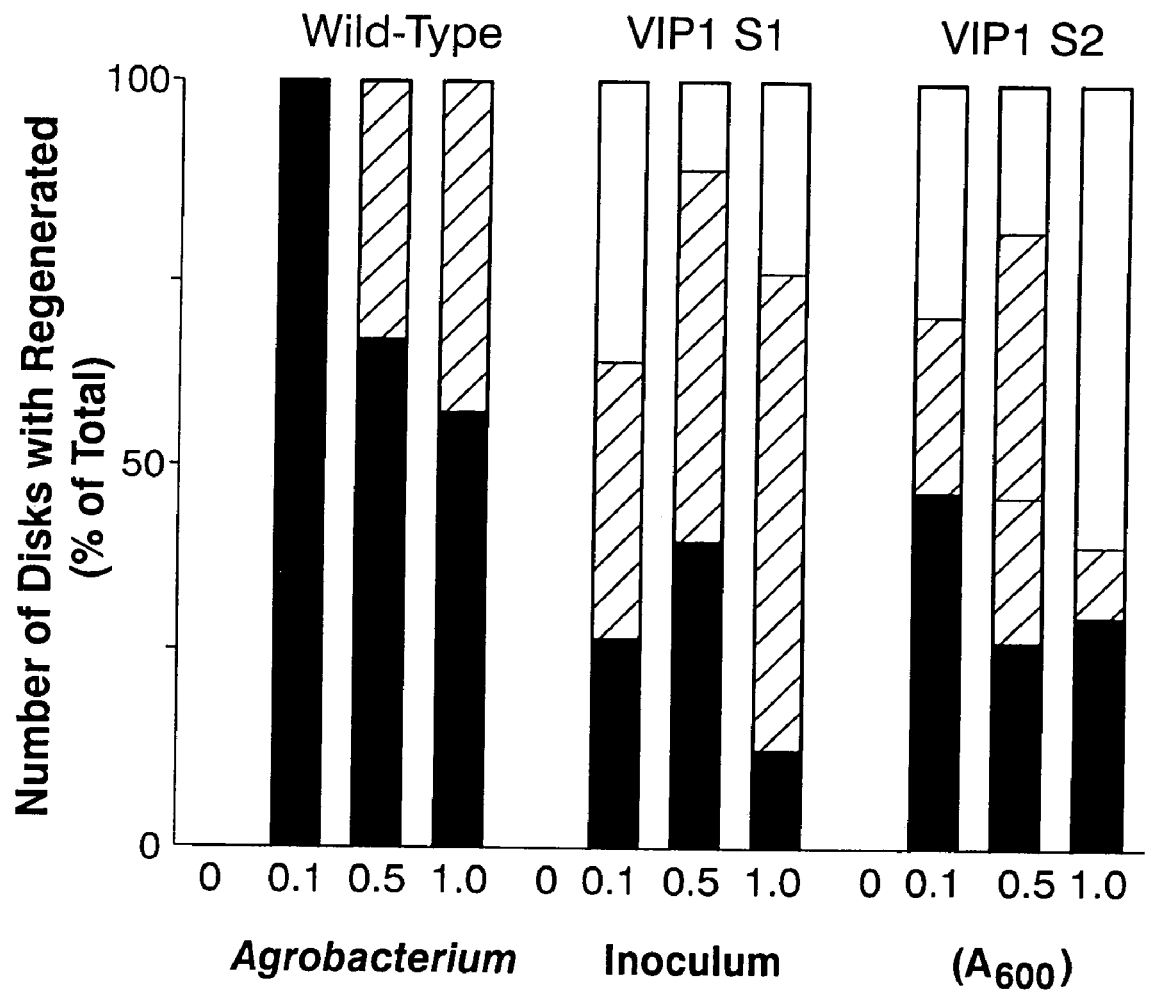
FIG. 2B graphically depicts increased Agrobacterium-mediated genetic transformation of VIP1 S1 and S2 plants and shows quantification of stable T-DNA expression. Black, gray, and white bars indicate the numbers of disks that developed 1-4, 5-9, and 10-20 shoots per disk, respectively. Total number of disks with regenerated shoots for each experimental condition was defined as 100%. All data represent three independent experiments with at least 20 disks per each experimental condition.

The increased susceptibility of the VIP1 plant lines to genetic transformation by *Agrobacterium* was quantified by counting the number of regenerated hygromycin-resistant shoots per each infected leaf disk tested. Similarly to quantification of transient expression (see FIG. 2A), these stable transformation data were classified into three groups: number of disks that gave rise to 1 to 4 shoots, 5 to 9 shoots, and 10-20 shoots per disk. FIG. 2B shows that while in the absence of *Agrobacterium* infection no shoots were formed, the wild-type plants infected with the lowest *Agrobacterium* inoculum produced an average of 2 shoots per disk (i.e., all disks fell into the first group of shoot numbers). At the highest inoculum used ($A_{600}$=1.0), only about 40% of the disks developed an average of 5 shoots per disk, corresponding to the second group of shoot numbers. However, under no conditions were wild-type leaf disks obtained that could be classified as the third group of shoot numbers (FIG. 2B). In contrast, both VIP1 S1 and VIP1 S2 plant lines produced higher numbers of shoots per disk. Indeed, at the $A_{600}$=1.0 inoculum, 85% of the disks from the VIP1 S1 plants and 70% of the disks from the VIP1 S2 plants developed more than 5 shoots, falling in the second and third categories of shoot numbers per leaf disk; in the third category alone, 25% and 60% of the disks from the VIP1 S1 and VIP1 S2 lines produced an average of 16 and 19 shoots per disk, respectively. At the bacterial inoculum of $A_{600}$=0.5, an average of 12 and 15 shoots per disk was observed in 10% and 20% of VIP1 S1 and VIP1 S2 plants, respectively. Finally, at the lowest inoculum ($A_{600}$=0.1), approximately 35% of disks from the VIP1 S1 plants and 40% of the disks from the VIP1 S2 plants developed an average of 13 and 14 shoots per disk, respectively. Collectively, these results suggest that overexpression of VIP1 in tobacco plants rendered them "super susceptible" to genetic transformation by *Agrobacterium*.

Figure 4A:
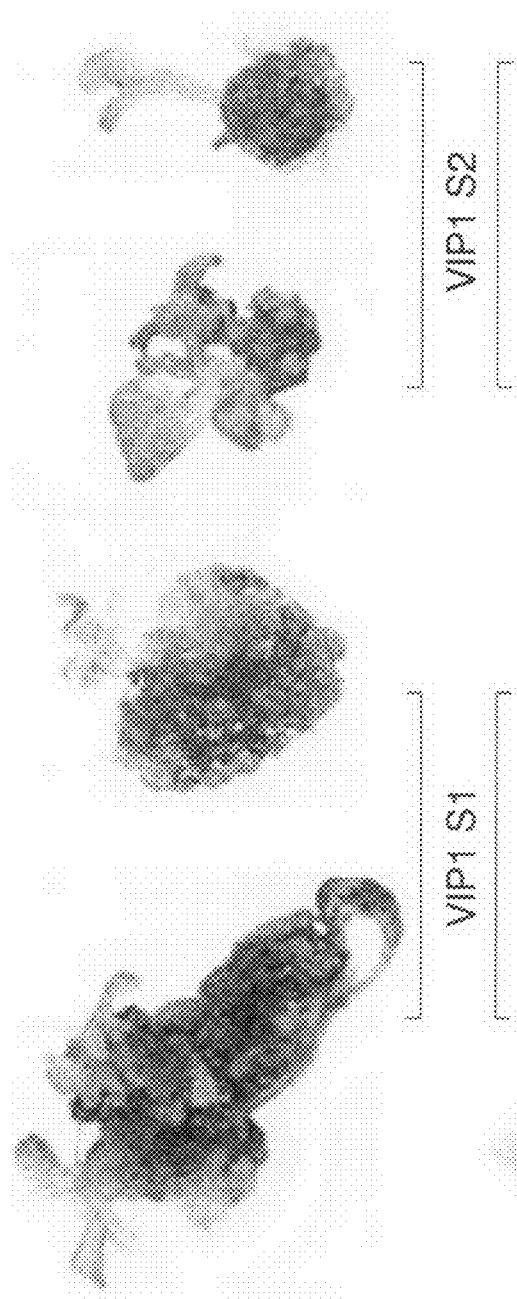
FIG. 4A shows GUS-staining of transgenic shoots regenerated from Agrobacterium-infected VIP1 S1 and VIP1 S2 lines regenerated on hygromycin-containing selective medium.
Figure 4B:
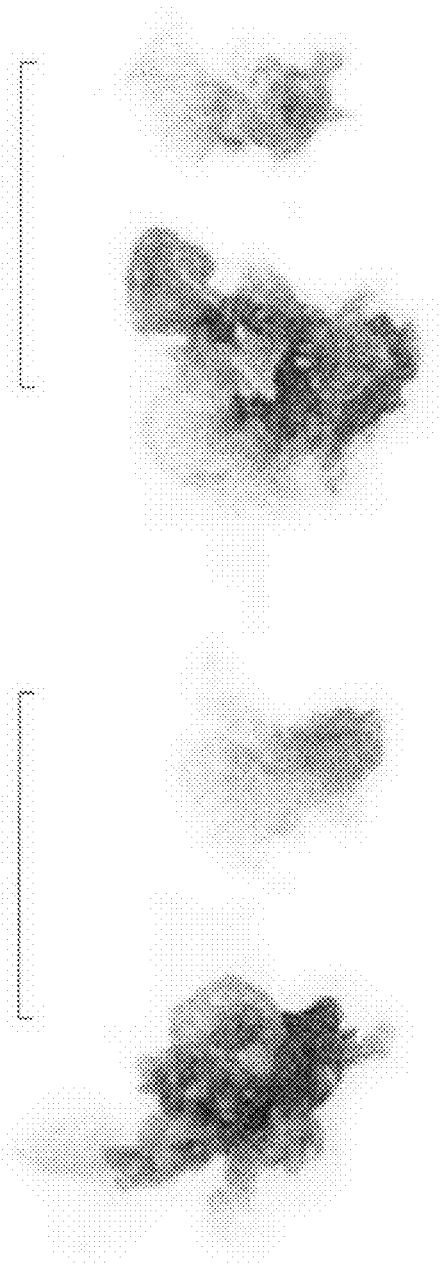
FIG. 4B shows shoots from uninfected VIP1 S1 and VIP1 S2 lines regenerated in the absence of selection.
Figure 6:
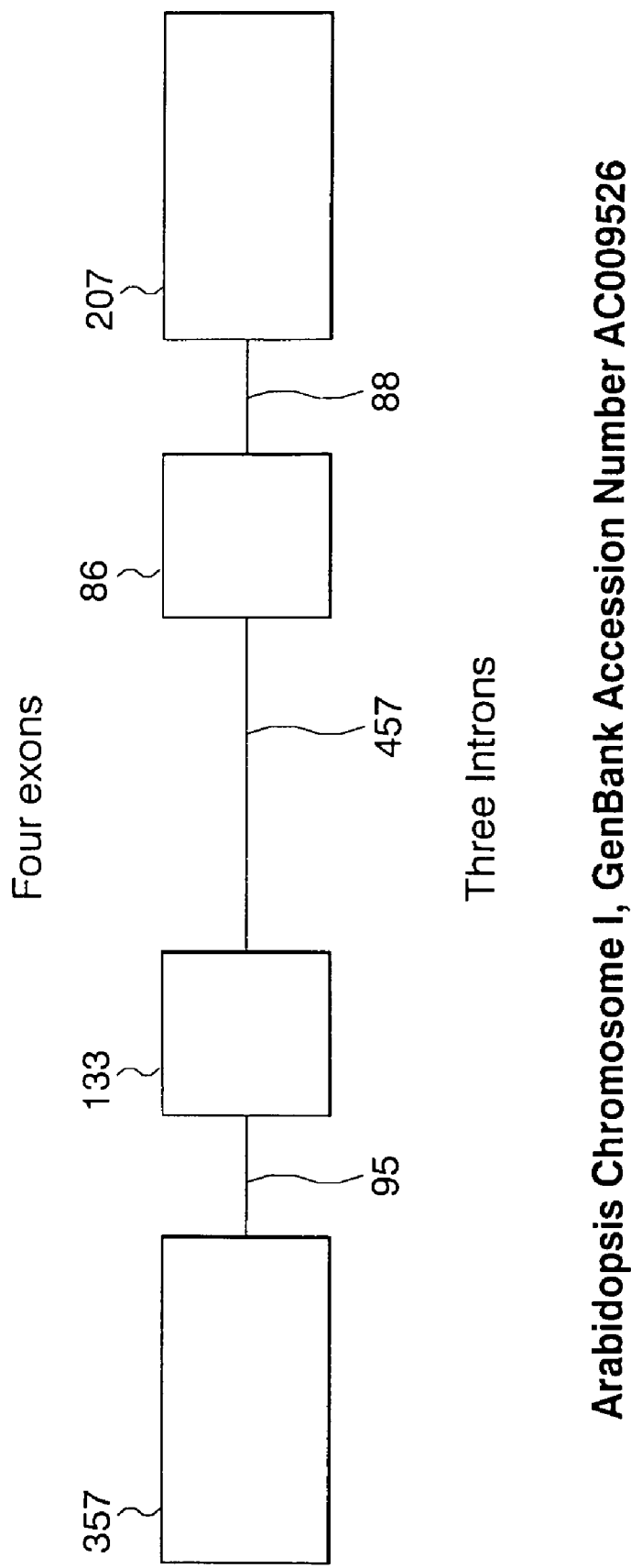
FIG. 6 shows the native VIP1 gene structure. The gene contains four exons and three introns.

That the shoots regenerated on the leaf disks derived from the VIP1 plants were indeed transgenic, i.e., resulted from the *Agrobacterium*-mediated genetic transformation, was inferred from their growth in the presence of hygromycin. However, besides the hpt gene coding for this antibiotic resistance, the transforming T-DNA also carried the uidA gene encoding the GUS enzymatic activity. Thus, in addition to hpi, the regenerated shoots are expected to carry the uidA transgene. To confirm the presence of uidA in the transgenic tissues, the shoots from VIP1 S1 and VIP1 S2 disks (see FIGS. 3A and B, respectively) were allowed to grow further into small plantlets, removed, and analyzed for the GUS activity by histochemical staining of the entire shoot and its cognate callus. FIG. 4A shows that the hygromycin-resistant shoots regenerated from *Agrobacterium*-infected VIP1 S1 and VIP1 S2 plant lines efficiently expressed the uidA transgene, resulting in the blue staining of the entire shoot. In control experiments, shoots regenerated from uninfected VIP1 plants in the absence of selection did not express GUS activity (FIG. 4B), indicating that the blue staining observed in the transformed shoots (FIG. 4A) was indeed due to the GUS activity and not to the presence of VIP1 in these tissues.

REFERENCES

1. Gaudin, V., Vrain, T. & Jouanin, L. Bacterial genes modifying hormonal balances in plants. *Plant Physiol. Biochem.* 32, 11-29 (1994).
2. Gelvin, S. B. *Agrobacterium* and plant genes involved in T-DNA transfer and integration. *Annu. Rev. Plant Physiol. Plant Mol. Biol.* 51, 223-256 (2000).
3. Tzfira, T., Rhee, Y., Chen, M.-H. & Citovsky, V. Nucleic acid transport in plant-microbe interactions: the molecules that walk through the walls. *Annu. Rev. Microbiol.* 54, 187-219 (2000).
4. Tzfira, T. & Citovsky, V. From host recognition to T-DNA integration: the function of bacterial and plant genes in the *Agrobacterium*-plant cell interaction. *Mol. Plant Pathol.* 1, 201-212 (2000).
5. Zupan, J., Muth, T. R., Draper, O. & Zambryski, P. C. The transfer of DNA from *Agrobacterium tumefaciens* into plants: a feast of fundamental insights. *Plant J.* 23, 11-28 (2000).
6. Piers, K. L., Heath, J. D., Liang, X., Stephens, K. M. & Nester, E. W. *Agrobacterium tumefaciens*-mediated transformation of yeast. *Proc. Natl. Acad. Sci. USA* 93, 1613-1618 (1996).
7. Bundock, P., den Dulk-Ras, A., Beijersbergen, A. & Hooykaas, P. J. J. Trans-kingdom T-DNA transfer from *Agrobacterium tumefaciens* to *Saccharomyces cerevisiae*. *EMBO J.* 14, 3206-3214 (1995).
8. Bundock, P. & Hooykaas, P. J. Integration of *Agrobacterium tumefaciens* T-DNA in the *Saccharomyces cerevisiae* genome by illegitimate recombination. *Proc. Natl. Acad. Sci. USA* 93, 15272-15275 (1996).
9. de Groot, M. J., Bundock, P., Hooykaas, P. J. & Beijersbergen, A. G. *Agrobacterium tumefaciens*-mediated transformation of filamentous fungi [published erratum appears in Nat. Biotechnol. 16, 1074 (1998)]. *Nat. Biotechnol.* 16, 839-842 (1998).
10. Kunik, T. et al. Genetic transformation of HeLa cells by *Agrobacterium*. *Proc. Natl. Acad. Sci. USA* 98, 1871-1876 (2001).
11. Bevan, M. W. Binary *Agrobacterium* vectors for plant transformation. *Nucleic Acids Res.* 12, 1811-1821 (1984).
12. Armitage, P., Walden, R. & Draper, J. in Plant Genetic Transformation and Gene Expression, A Laboratory Manual. (eds. J. Draper, R. Scott, P. Armitage & R. Walden) 1-67 (Blackwell Scientific Publications Ltd., London; 1988).
13. Gelvin, S. B. The introduction and expression of transgenes in plants. *Curr. Opin. Biotechnol.* 9, 227-232 (1998).
14. Liu, C. N., Li, X. Q. & Gelvin, S. B. Multiple copies of virG enhance the transient transformation of celery, carrot, and rice tissues by *Agrobacterium turmfaciens*. *Plant Mol. Biol.* 20, 1071-1087 (1992).
15. Wang, K., Herrera-Estrella, A. & Van Montagu, M. Overexpression of virD1 and virD2 genes in *Agrobacterium tumefaciens* enhances T-complex formation and plant transformation. *J. Bacteriol.* 172, 4432-4440 (1990).
16. Jin, S. G., Komari, T., Gordon, M. P. & Nester, E. W. Genes responsible for the supervirulence phenotype of *Agrobacterium tumefaciens* A281. *J. Bacteriol.* 169, 4417-4425 (1987).
17. Newell, C. A. Plant transformation technology. Developments and applications. *Mol Biotechnol.* 16, 53-65 (2000).

18. Tzfira, T., Vadiya, M. & Citovsky, V. VIP1, an *Arabidopsis* protein that interacts with *Agrobacterium* VirE2, is involved in VirE2 nuclear import and *Agrobacterium* infectivity. *EMBO J.* 20, 3596-3607 (2001).
19. Zambryski, P. C. Chronicles from the *Agrobacterium*-plant cell DNA transfer story. *Annu. Rev. Plant Physiol. Plant Mol. Biol.* 43, 465-490 (1992).
20. Zupan, J. & Zambryski, P. C. The *Agrobacterium* DNA transfer complex. *Crit. Rev. Plant Sci.* 16, 279-295 (1997).
21. Howard, E. A., Citovsky, V. & Zambryski, P. C. The T-complex of *Agrobacterium tumefaciens*. *UCLA Symp. Mol. Cell Biol.* 129, 1-11 (1990).
22. Ward, D., Zupan, J. & Zambryski, P. C. *Agrobacterium* VirE2 gets the VIP1 treatment in plant nuclear import. *Trends Plant Sci.* 7, 1-3 (2002).
23. Janssen, B. J. & Gardner, R. C. Localized transient expression of GUS in leaf discs following cocultivation with *Agrobacterium*. *Plant Mol. Biol.* 14, 61-72 (1990).
24. Nam, J. et al. Identification of T-DNA tagged *Arabidopsis* mutants that are resistant to transformation by *Agrobacterium*. *Mol. Gen. Genet.* 261, 429-438 (1999).
25. Tzfira, T. et al. Transgenic Populus: a step-by-step protocol for its *Agrobacterium*-mediated transformation. *Plant Mol. Biol. Rep.* 15, 219-235 (1997).
26. Horsch, R. B. et al. A simple and general method for transferring genes into plants. *Science* 227, 1229-1231 (1985).
27. Tzfira, T. & Citovsky, V. Partners-in-infection: host proteins involved in the transformation of plant cells by *Agrobacterium*. *Trends Cell Biol.* 12, 121-129 (2002).
28. van der Krol, A. R. & Chua, N.-H. The basic domain of plant B-ZIP proteins facilitates import of a reporter protein into plant nuclei. *Plant Cell* 3, 667-675 (1991).
29. Citovsky, V., Guralnick, B., Simon, M. N. & Wall, J. S. The molecular structure of *Agrobacterium* VirE2-single stranded DNA complexes involved in nuclear import. *J Mol. Biol.* 271, 718-727 (1997).
30. Gallie, D. R., Lucas, W. J. & Walbot, V. Visualizing mRNA expression in plant protoplasts: factors influencing efficient mRNA uptake and translation. *Plant Cell* 1, 303-311 (1989).
31. Murashige, T. & Skoog, F. A revised medium for rapid growth and bio assays with tobacco tissue cultures. *Physiolog. Plant.* 15, 473-497 (1962).
32. Carrington, J. C., Freed, D. D. & Leinicke, A. J. Bipartite signal sequence mediates nuclear translocation of the plant potyviral NIa protein. *Plant Cell* 3, 953-962 (1991).
33. Ausubel, F. M. et al. Current Protocols in Molecular Biology. (Greene Publishing-Wiley Interscience, New York; 1987).

What is claimed is:

1. A chimeric gene construct consisting of, in the 5' to 3' direction, a promoter which functions in a plant cell operably linked to a coding sequence encoding a VIP1 protein, said VIP1 protein consisting of the amino acid sequence of SEQ ID NO:2.

2. A chimeric gene construct consisting of, in the 5' to 3' direction, a promoter which functions in a plant cell operably linked to a coding sequence encoding a VIP1 protein, said VIP1 protein consisting of the amino acid sequence of SEQ ID NO:2 and a 3' regulatory region which functions in a plant cell, operably linked to the 3' end of the coding sequence.

3. A vector comprising the chimeric gene construct of claim 1 or 2.

4. A transgenic plant cell or a transgenic plant regenerated therefrom which over-expresses a VIP1, wherein said plant or plant cell is transformed with the construct of claim 1 or claim 2.

5. The transgenic plant cell or plant regenerated therefrom of claim 4 which further expresses a transgene introduced into the plant cell via *Agrobacterium*-mediated transformation.

6. The transgenic plant cell or plant regenerated therefrom of claim 5 wherein the transgene is native with respect to the plant or plant cell.

7. The transgenic plant cell or plant regenerated therefrom of claim 5 wherein the trans gene is foreign with respect to the plant or plant cell.

8. Transgenic progeny of the transgenic plant of claim 4; wherein said progeny comprises said construct.

9. Propagation material of the transgenic plant of claim 4; wherein said propagation material comprises said construct.

10. The propagation material of claim 9 selected from the group consisting of pollen, ovum, seeds, tubers, roots, and cuttings.

11. Cut flowers of the transgenic plant of claim 4.

12. Cut flowers from the transgenic progeny of claim 8.

13. The chimeric gene construct of claim 1 or 2 wherein the coding sequence consists of the sequence of SEQ ID NO:1.

14. A method of increasing susceptibility of a plant cell to *Agrobacterium* infection, said method comprising: introducing into a plant cell the construct of claim 1 or claim 2.

15. The method of claim 14 wherein the plant cell is from a monocotyledonous plant species.

16. The method of claim 14 wherein the plant cell is from a dicotyledonous plant species.

17. A method of improving *Agrobacterium*-mediated gene transfer, said method comprising introducing into a plant cell the construct of claim 1 or claim 2 and transforming the plant cell with an *Agrobacterium* transformation vector.

18. The method of claim 17 wherein the *Agrobacterium* transformation vector comprises the *Agrobacterium* Vir region and wherein a gene of interest is positioned between the right and left border sequences of *Agrobacterium* T-DNA.

19. The method of claim 17 wherein the plant cell is transformed with the *Agrobacterium* transformation vector simultaneously with the construct encoding the VIP protein.

20. The method of claim 17 wherein the plant cell is transformed with the *Agrobacterium* transformation vector following transformation of the plant cell with the construct encoding the VIP protein.

21. The method of claim 17 wherein the plant cell is from a monocotyledonous plant species.

22. The method of claim 17 wherein the plant cell is from a dicotyledonous plant species.

* * * * *